United States Patent [19]
Martin et al.

[11] Patent Number: 6,054,475
[45] Date of Patent: Apr. 25, 2000

[54] SUBSTITUTED DIHYDROBENZOFURAN-BASED PHOSPHODIESTERASE 4 INHIBITORS USEFUL FOR TREATING AIRWAY DISORDERS

[75] Inventors: Thomas Martin; Wolf-Rüdiger Ulrich, both of Konstanz, Germany

[73] Assignee: Byk Gulden Lomberg Chemische Fabrik GmbH, Konstanz, Germany

[21] Appl. No.: 09/284,459

[22] PCT Filed: Nov. 11, 1997

[86] PCT No.: PCT/EP97/06248

§ 371 Date: Apr. 16, 1999

§ 102(e) Date: Apr. 16, 1999

[87] PCT Pub. No.: WO98/22453

PCT Pub. Date: May 28, 1998

[30] Foreign Application Priority Data

Nov. 20, 1996 [DE] Germany ............ 196 47 881
Nov. 22, 1996 [AT] Austria ................ 96118743

[51] Int. Cl.⁷ ............. A61K 31/343; A61K 31/382; C07D 307/79; C07D 309/04; C07D 335/02
[52] U.S. Cl. ............. 514/432; 514/462; 540/543; 540/597; 546/268.1; 548/409; 549/28; 549/331; 549/345; 549/414; 549/469
[58] Field of Search ............. 540/543, 597; 546/268.1; 548/409; 549/331, 28, 345, 414, 469; 514/432, 462

[56] References Cited

U.S. PATENT DOCUMENTS

| | | | |
|---|---|---|---|
| 5,552,438 | 9/1996 | Christensen, IV | 514/520 |
| 5,602,157 | 2/1997 | Christensen, IV | 514/362 |
| 5,614,540 | 3/1997 | Christensen, IV | 514/362 |
| 5,643,946 | 7/1997 | Christensen, IV | 514/512 |

FOREIGN PATENT DOCUMENTS

WO 93/19749  10/1993  WIPO ............ A61K 31/275

*Primary Examiner*—Johann Richter
*Assistant Examiner*—Taofiq A. Solola
*Attorney, Agent, or Firm*—Jacobson, Price, Holman & Stern, PLLC

[57] ABSTRACT

Compounds of formula (I)

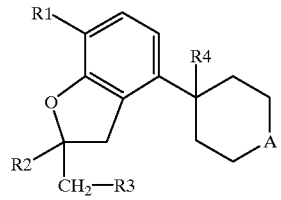

and the salts of these compounds, are efficacious PDE (phosphodiesterase) inhibitors.

15 Claims, 3 Drawing Sheets

FORMULA SHEET I
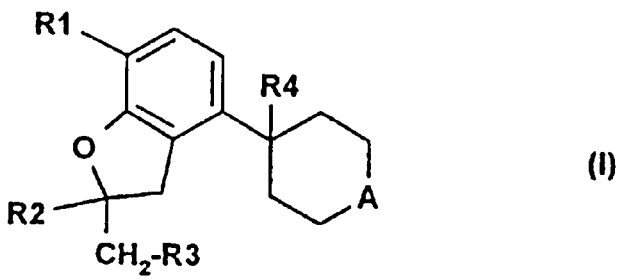
(I)
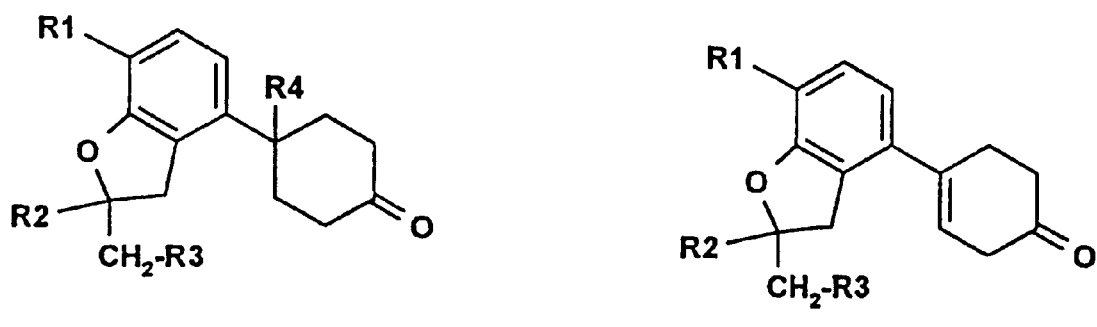
(II)　　　　　　　　　　　(III)
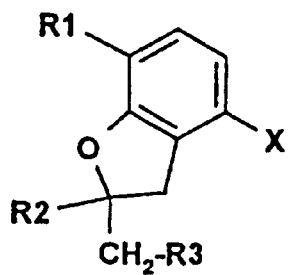
(IV)

FORMULA SHEET II
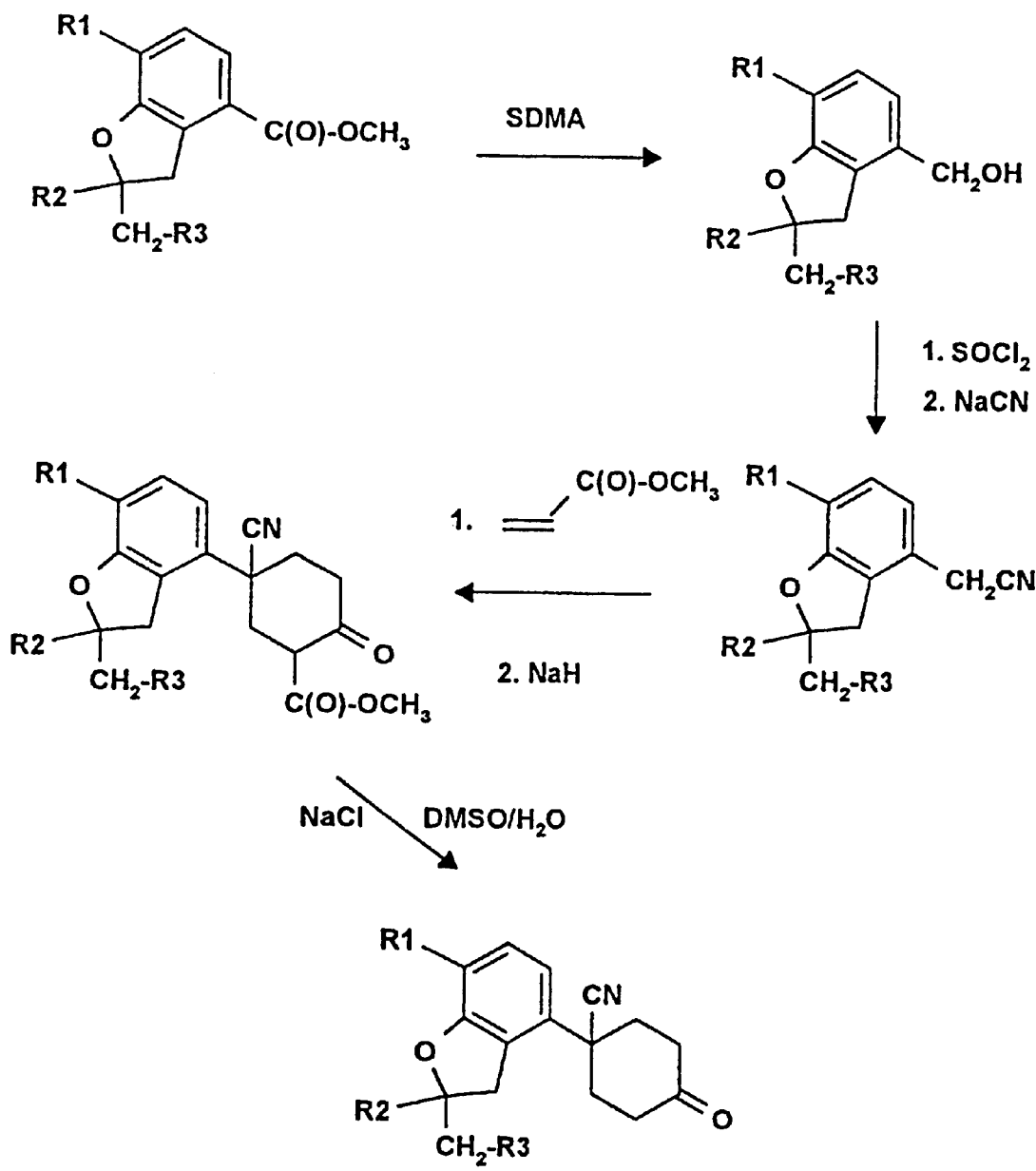

FORMULA SHEET II a
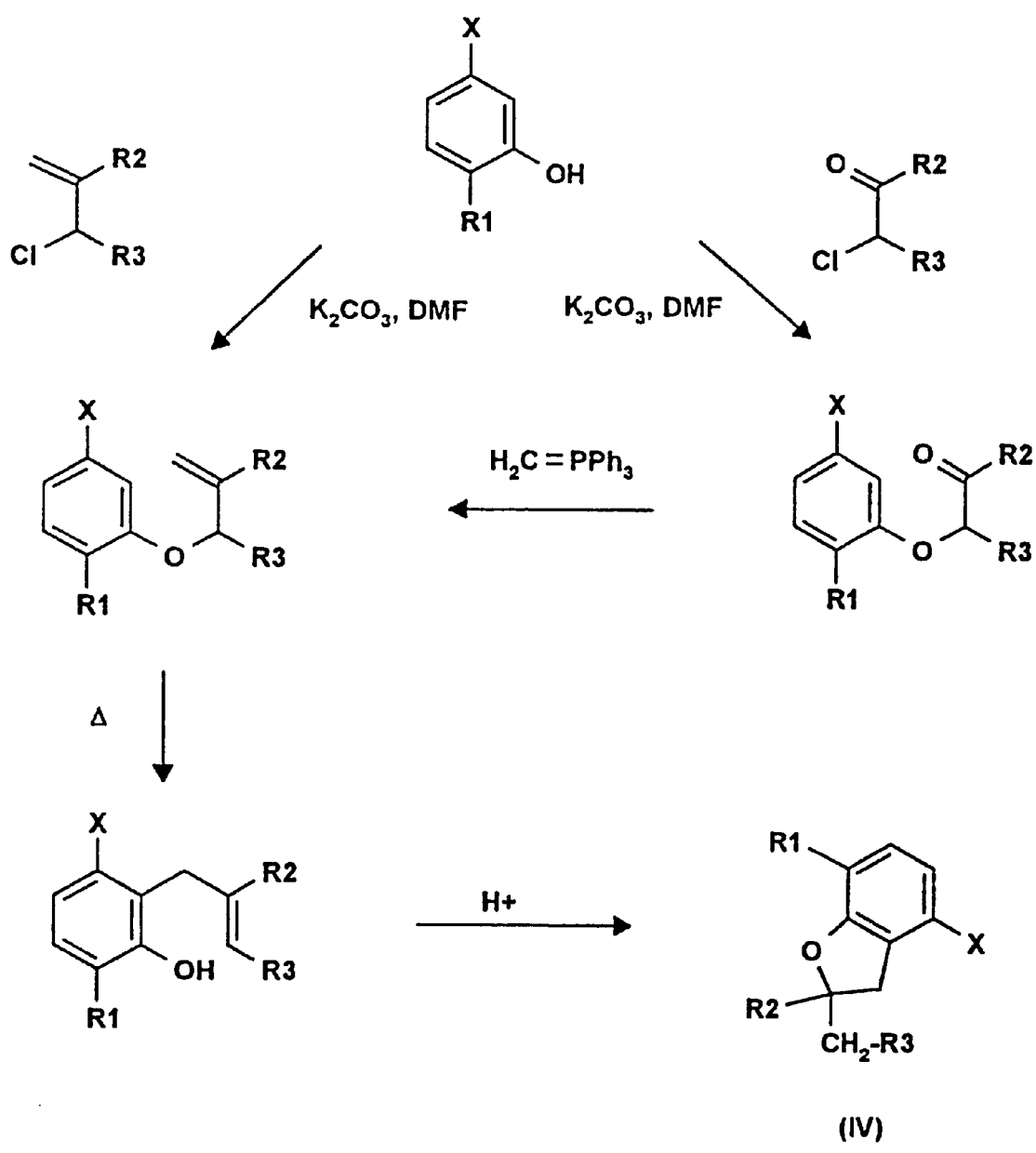

SUBSTITUTED DIHYDROBENZOFURAN-BASED PHOSPHODIESTERASE 4 INHIBITORS USEFUL FOR TREATING AIRWAY DISORDERS

RELATED APPLICATIONS

This application is a 371 of PCT/EP97/06248 filed Nov. 11, 1997. This application is related to co-pending application Ser. No. 08/952,275, filed Nov. 18, 1997.

TECHNICAL FIELD

The invention relates to novel compounds which are used in the pharmaceutical industry for the production of medicaments.

1. Known Technical Background

International Patent Application WO92/12961 describes benzamides having PDE-inhibiting properties. International Patent Applications WO93/25517 and WO93/19749 disclose trisubstituted phenyl derivatives as selective PDE4 inhibitors. International Patent Application WO94/02465 describes inhibitors of c-AMP phosphodiesterase (PDE) and of tumor necrosis factor (TNF).

2. Description of the Invention

It has been found that the dihydrobenzofurans described below in greater detail, which differ from the previously published compounds by a different type of substitution, have surprising and particularly advantageous properties.

The invention thus relates to compounds of the formula I (see attached formula sheet I), in which R1 is 1–6C-alkoxy, 3–7C-cycloalkoxy, 3–7C-cycloalkylmethoxy, benzyloxy or 1–4C-alkoxy which is completely or predominantly substituted by fluorine, R2 is 1–4C-alkyl and R3 is hydrogen or 1–4C-alkyl.

or in which

R2 and R3, together and including the two carbon atoms to which they are bonded, are a spiro-linked 5-, 6- or 7-membered hydrocarbon ring, if desired interrupted by an oxygen atom or an imino (—NH—) group, R4 is hydrogen, hydroxyl, nitro, cyano, carboxyl, 1–4C-alkoxy or 1–4C-alkoxycarbonyl, A is B, —CH(R5)— or >C=N—R6, where B is oxygen (—O—), imino (—NH—), sulfinyl (—S (O)—), sulfonyl (—S (O)$_2$—) or carbonylimino (—C (O)NH—) and R5 is carboxyl, 1–4C-alkoxycarbonyl, aminocarbonyl, mono- or di-1–4C-alkylaminocarbonyl, hydroxylaminocarbonyl (—C(O)NHOH), 1–4C-alkoxyaminocarbonyl or a radical of the formula (a)

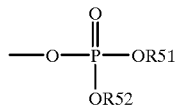

(a)

where

R51 is hydrogen, 1–4C-alkyl or aryl and

R52 is hydrogen, 1–4C-alkyl or aryl, where aryl is a phenyl, pyridyl, benzyl or phenethyl radical which can be unsubstituted or mono- or disubstituted by hydroxyl, 1–4C-alkoxy, halogen, amino, cyano or nitro, R6 is hydroxyl or 1–4C-alkylcarbonyloxy, and the salts of these compounds.

1–4C-Alkyl represents straight-chain or branched alkyl radicals having 1 to 4 carbon atoms. Examples which may be mentioned are the butyl, isobutyl, sec-butyl, tert-butyl, propyl, isopropyl, ethyl and methyl radicals.

1–6C-Alkoxy represents a radical which, in addition to the oxygen atom, contains a straight-chain or branched alkyl radical having 1 to 6 carbon atoms. Alkoxy radicals having 1 to 6 carbon atoms which may be mentioned, for example, are the hexyloxy, isohexyloxy (4-methylpentyloxy), neohexyloxy (3,3-dimethylbutoxy), pentyloxy, isopentyloxy (3-methylbutoxy), neopentyloxy (2,2-dimethylpropoxy), butoxy, isobutoxy, sec-butoxy, tert-butoxy, propoxy, isopropoxy, ethoxy and methoxy radicals.

3–7C-Cycloalkoxy represents cyclopropyloxy, cyclobutyloxy, cyclopentyloxy, cyclohexyloxy and cycloheptyloxy, of which cyclopropyloxy, cyclobutyloxy and cyclopentyloxy are preferred.

3–7C-Cycloalkylmethoxy represents cyclopropylmethoxy, cyclobutylmethoxy, cyclopentylmethoxy, cyclohexylmethoxy and cycloheptylmethoxy, of which cyclopropylmethoxy, cyclobutylmethoxy and cyclopentylmethoxy are preferred.

1–4C-Alkoxy which is completely or predominantly substituted by fluorine and which may be mentioned, for example, is the 2,2,3,3,3-pentafluoropropoxy, the perfluoroethoxy, the 1,1,2,2-tetrafluoroethoxy, the 1,2,2-trifluoroethoxy, the trifluoromethoxy, in particular the 2,2,2-trifluoroethoxy, and preferably the difluoromethoxy radical.

A spiro-linked, 5-, 6- or 7-membered hydrocarbon ring, if desired interrupted by an oxygen atom or an imino (—NH—) group, which may be mentioned is the cyclopentane, the cyclohexane, the cycloheptane, the tetrahydrofuran, the tetrahydropyran or the piperidine ring.

1–4C-Alkoxy represents a radical which, in addition to the oxygen atom, contains one of the above-mentioned 1–4C-alkyl radicals. Examples which may be mentioned are the methoxy and the ethoxy radicals.

1–4C-Alkoxycarbonyl represents a carbonyl group to which one of the abovementioned 1–4C-alkoxy radicals is bonded. Examples which may be mentioned are the methoxycarbonyl radical (CH$_3$O—C(O)—) and the ethoxycarbonyl radical (CH$_3$CH$_2$O—C(O)—).

In addition to the carbonyl group, mono- or di-1–4C-alkylaminocarbonyl radicals contain a mono- or di- 1–4C-alkylamino radical. Examples which may be mentioned are the N-methyl-, the N,N-dimethyl-, the N-ethyl-, the N-propyl-, the N,N-diethyl- and the N-isopropylaminocarbonyl radicals.

A 1–4C-alkoxyaminocarbonyl radical which may be mentioned is, for example, the methoxyaminocarbonyl radical (—C(O)NHOCH$_3$).

1–4C-Alkylcarbonyloxy represents a carbonyloxy group to which one of the abovementioned 1–4C-alkyl radicals is bonded. An example which may be mentioned is the acetoxy radical (CH$_3$C(O)—O—).

Suitable salts of compounds of the formula I—depending on substitution—are all acid addition salts or all salts with bases. Particular mention may be made of the pharmacologically tolerable salts of the inorganic and organic acids customarily used in pharmacy. Those suitable are, on the one hand, water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4- hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, where the acids are employed in salt preparation—depending on whether a mono- or polybasic acid is concerned and depending on which salt is desired—in an equimolar quantitative ratio or one differing therefrom.

On the other hand, salts with bases are also suitable. Examples of salts with bases which may be mentioned are alkali metal (lithium, sodium, potassium) or calcium, aluminum, magnesium, titanium, ammonium, meglumine or guanidinium salts, where here too the bases are employed in salt preparation in an equimolar quantitative ratio or one differing therefrom.

Pharmacologically intolerable salts, which can be initially obtained as process products, for example, in the preparation of the compounds according to the invention on an industrial scale, are converted into pharmacologically tolerable salts by processes known to the person skilled in the art.

According to expert's knowledge the compounds of the invention as well as their salts may contain, e.g. when isolated in crystalline form, varying amounts of solvents. Included within the scope of the invention are therefore all solvates and in particular all hydrates of the compounds of formula I as well as all solvates and in particular all hydrates of the salts of the compounds of formula I.

Compounds of the formula I to be emphasized are, on the one hand, those in which R1 is 1–6C-alkoxy, 3–7C-cycloalkoxy, 3–7C-cycloalkylmethoxy, benzyloxy or 1–4C-alkoxy which is completely or predominantly substituted by fluorine, R2 is 1–4C-alkyl and R3 is hydrogen or 1–4C-alkyl, or in which R2 and R3, together and including the two carbon atoms to which they are bonded, are a spiro-linked 5-, 6- or 7-membered hydrocarbon ring, if desired interrupted by an oxygen atom or an imino (—NH—) group, R4 is hydrogen, hydroxyl, nitro, cyano, carboxyl, 1–4C-alkoxy or 1–4C-alkoxycarbonyl, A is B, —CH(R5)— or >C=N—R6, where B is oxygen (—O—), imino (—NH—), sulfinyl (—S(O)—), sulfonyl (—S(O)$_2$—) or carbonylimino (—C(O)NH—) and R5 is aminocarbonyl, mono- or di-1–4C-alkylaminocarbonyl, hydroxylaminocarbonyl(—C(O)NHOH), 1–4C-alkoxyaminocarbonyl or a radical of the formula (a)

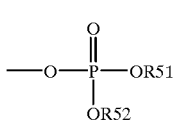

(a)

where

R51 is hydrogen, 1–4C-alkyl or aryl and

R52 is hydrogen, 1–4C-alkyl or aryl, where aryl is a phenyl, pyridyl, benzyl or phenethyl radical which can be unsubstituted or mono- or disubstituted by hydroxyl, 1–4C-alkoxy, halogen, amino, cyano or nitro;

R6 is hydroxyl or 1–4C-alkylcarbonyloxy, and the salts of these compounds and the following compounds of the formula I mentioned by name and their salts:

Methyl cis-4-cyano-4-(2,3-dihydro-7-methoxybenzofuran-2-spiro-1'-cyclopentan-4-yl)cyclohexane-1-carboxylate, cis-4-Cyano-4-(2,3-dihydro-7-methoxybenzofuran-2-spiro-1'-cyclopentan4-yl)cyclohexane-1-carboxylic acid and cis-4-Cyano-4-(2,3-dihydro-7-methoxybenzofuran-2-spiro-4'-tetrahydropyran-4-yl)cyclohexane-1-carboxylic acid.

Compounds of the formula I to be emphasized are, on the other hand, those in which R1 is 1–6C-alkoxy, 3–7C-cycloalkoxy, 3–7C-cycloalkylmethoxy, benzyloxy or 1–4C-alkoxy which is completely or predominantly substituted by fluorine, R2 is 1–4C-alkyl and R3 is hydrogen or 1–4C-alkyl, or in which R2 and R3, together and including the two carbon atoms to which they are bonded, are a spiro-linked 5-, 6- or 7-membered hydrocarbon ring, if desired interrupted by an oxygen atom or an imino (—NH—) group, R4 is hydroxyl or 1–4C-alkoxy, A is —CH(R5)—, where R5 is carboxyl or 1–4C-alkoxycarbonyl, and the salts of these compounds.

One embodiment of the compounds of the formula I to be emphasized are those compounds in which R1 is 1–6C-alkoxy, 3–7C-cycloalkoxy, 3–7C-cycloalkylmethoxy, benzyloxy or 1–4C-alkoxy which is completely or predominantly substituted by fluorine, R2 is 1–4C-alkyl and R3 is hydrogen or 1–4C-alkyl, or in which R2 and R3, together and including the two carbon atoms to which they are bonded, are a spiro-linked 5-, 6- or 7-membered hydrocarbon ring, if desired interrupted by an oxygen atom or an imino (—NH—) group, R4 is hydrogen, hydroxyl, nitro, cyano, carboxyl, 1–4C-alkoxy or 1–4C-alkoxycarbonyl A is B, —CH(R5)— or >C=N—R6, where B is oxygen (—O—), imino (—NH—), sulfinyl (—S(O)—), sulfonyl (—S(O)$_2$—) or carbonylimino (—C(O)NH—) and R5 is aminocarbonyl, hydroxylaminocarbonyl (—C(O)NHOH), 1–4C-alkoxyaminocarbonyl or a radical of the formula (a)

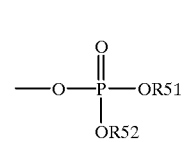

(a)

where

R51 is hydrogen, 1–4C-alkyl or aryl and

R52 is hydrogen, 1–4C-alkyl or aryl, where aryl is a phenyl or benzyl radical which can be unsubstituted or mono- or disubstituted by 1–4C-alkoxy, halogen or nitro, R6 is hydroxyl or 1–4C-alkylcarbonyloxy, and the salts of these compounds.

Compounds of the formula I particularly to be emphasized are those in which

R1 is 1–4C-alkoxy, 3–5C-cycloalkoxy or 1–2C-alkoxy which is completely or predominantly substituted by fluorine, R2 is 1–4C-alkyl and R3 is hydrogen or 1–4C-alkyl, or in which R2 and R3, together and including the two carbon atoms to which they are bonded, are a spiro-linked cyclopentane, cyclohexane, tetrahydrofuran or tetrahydropyran ring, R4 is hydrogen, hydroxyl, cyano, carboxyl, 1–2C-alkoxy or 1–2C-alkoxycarbonyl, A is B, —CH(R5)— or >C=N—R6, where B is oxygen (—O—), sulfinyl(—S(O)—), sulfonyl (—S(O)$_2$—) or carbonylimino (—C(O)NH—) and R5 is aminocarbonyl, hydroxylaminocarbonyl (—C(O)NHOH) or a radical of the formula (a)

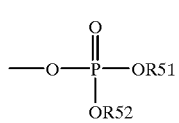

(a)

where

R51 is hydrogen, 1–2C-alkyl or aryl and

R52 is hydrogen, 1–2C-alkyl or aryl, where aryl is a phenyl or benzyl radical which can be unsubstituted or monosubstituted by methoxy or halogen, R6 is hydroxyl or 1–2C-alkylcarbonyloxy, and the salts of these compounds.

Preferred compounds of the formula I are those in which

R1 is 1–4C-alkoxy,

R2 and R3, together and including the two carbon atoms to which they are bonded, are a spiro-linked cyclopentane or tetrahydropyran ring, R4 is hydroxyl, cyano or methoxy, A is B, —CH(R5)— or >C=N—R6, where B is oxygen (—O—), sulfonyl (—S(O)$_2$—) or carbonylimino (—C(O)NH—) and R5 is aminocarbonyl, hydroxylaminocarbonyl or a radical of the formula (a)

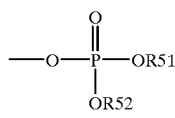

(a)

where

R51 is phenyl,

R52 is hydrogen,

R6 is hydroxyl or acetoxy, and the salts of these compounds.

Particularly preferred compounds of the formula I are those in which

R1 is methoxy and

R2 and R3, together and including the two carbon atoms to which they are bonded, are a spiro-linked cyclopentane or tetrahydropyran ring, R4 is cyano or methoxy, A is B, —CH(R5)— or >C=N—R6, where B is oxygen (—O—), sulfonyl (—S(O)$_2$—) or carbonylimino(—C(O)NH—) and R5 is aminocarbonyl, hydroxylaminocarbonyl or a radical of the formula (a)

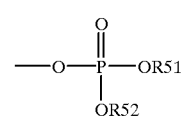

(a)

where

R51 is phenyl,

R52 is hydrogen,

R6 is hydroxyl, and the salts of these compounds.

Further particularly preferred compounds of the formula I which may be mentioned are:

Methyl cis-4-cyano-4-(2,3-dihydro-7-methoxybenzofuran-2-spiro-1'-cyclopentan-4-yl)cyclohexane-1-carboxylate, cis-4-Cyano-4-(2,3-dihydro-7-methoxybenzofuran-2-spiro-1'-cyclopentan-4-yl)cyclohexane-1-carboxylic acid and cis-4-Cyano-4-(2,3-dihydro-7-methoxybenzofuran-2-spiro-4'-tetrahydropyran-4-yl)cyclohexane-1-carboxylic acid, and the salts of the carboxylic acids with bases.

The compounds of the formula I can be present as cis or trans isomers and—if the substituents —R2 and —CH$_2$R3 are not identical—they are also chiral compounds. The invention therefore comprises both all pure diastereomers and pure enantiomers and their mixtures in any mixing ratio including the racemates. However, the compounds of the formula I are preferred in which the substituents —R2 and —CH$_2$R3 are identical.

The enantiomers can be separated in a manner known per se (for example by preparation and separation of appropriate diastereoisomeric compounds).

The invention further relates to processes for the preparation of the compounds of the formula I and their salts.

Compounds of the formula I in which A is —CH(R5)—, R1, R2, R3 and R4 have the meanings indicated above and R5 is carboxyl can be prepared, for example, by hydrolyzing compounds of the formula I in which A is —CH(R5)—, R1, R2, R3 and R4 have the meanings indicated above and R5 is alkoxycarbonyl, and if desired then converting compounds of the formula I obtained into their salts, or by converting salts of the compounds of the formula I obtained into the free compounds.

If desired, further compounds of the formula I can be converted into other compounds of the formula I by derivatization (in particular of the radicals R4 and R5) in a manner known to the person skilled in the art or as described in the following examples. In this manner, for example, compounds of the formula I in which R1, R2, R3 and R4 have the meanings indicated above, A is —CH(R5)— and R5 is aminocarbonyl, mono- or dialkylaminocarbonyl, alkoxyaminocarbonyl or hydroxylaminocarbonyl are also accessible.

The hydrolysis of compounds of the formula I in which A is —CH(R5)— and R5 is alkoxycarbonyl is carried out by the use of methods known to the person skilled in the art, e.g. as described in the following examples.

Compounds of the formula I in which A is —CH(R5)—, R1, R2, R3 and R4 have the meanings indicated above and R5 is alkoxycarbonyl are obtained, for example, by solvolysis of corresponding compounds of the formula I, in which A is

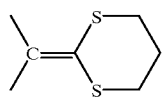

The solvolysis is preferably carried out in an absolute alcohol as a solvent under acidic conditions in the presence of a mercury salt, such as, for example, mercury(II) chloride.

Compounds of the formula I in which A is

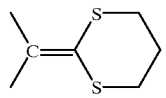

and R1, R2, R3 and R4 have the meanings indicated above, can be prepared, for example, from the corresponding compounds of the formula II (see attached formula sheet I) by reaction with 2-lithium-2-trimethylsilyl-1,3-dithiane.

The reaction is expediently carried out in an inert solvent such as, for example, n-hexane, diethyl ether or tetrahydrofuran or mixtures thereof at low temperatures (preferably −60° to −100° C.) under a protective gas atmosphere.

Compounds of the formula II in which R1, R2 and R3 have the abovementioned meanings and R4 is cyano can be prepared, for example, by the use of known methods, starting from corresponding compounds of the formula IV (see attached formula sheet I) in which X is the group —C(O)OCH$_3$, according to the general reaction scheme on the attached formula sheet II. The reaction sequence is described by way of example under "starting compounds"; the preparation of further compounds can be carried out analogously.

The compounds of the formula IV in which R1, R2 and R3 have the abovementioned meanings and X is halogen or the group —C(O)—OCH$_3$ can be prepared according to the general reaction scheme on the attached formula sheet IIa. The synthesis of compounds of the formula IV is described by way of example under "starting compounds". Further compounds of the formula IV can be prepared in an analogous manner.

Compounds of the formula II in which R1, R2 and R3 have the abovementioned meanings and R4 is hydrogen can be prepared by selective hydrogenation of the carbon double bond in the cyclohexene ring of corresponding compounds of the formula III (see attached formula sheet I).

Compounds of the formula III in which R1, R2 and R3 have the abovementioned meanings are accessible, for example, by addition of corresponding compounds of the formula IV, in which X has the meaning lithium, to 1,4-cyclohexanedione and subsequent elimination of water. Expediently, the 1,4-cyclohexanedione is employed in partly protected form, for example as a monoethylene ketal, and the protective group is removed again after reaction has taken place.

Compounds of the formula IV in which X is lithium are accessible from corresponding compounds of the formula IV in which X is halogen, in particular bromine, by metal-halogen exchange.

Compounds of the formula I in which R1, R2 and R3 have the abovementioned meanings, R4 is cyano and A is —CH(R5)—, where R5 is phosphate, mono- or dialkyl phosphate or mono- or diaryl phosphate, can be prepared by reaction of the corresponding compounds of the formula I in which A is —CH(OH)— with suitable phosphorylating reagents.

Suitable phosphorylating reagents which may be mentioned are, for example, diethyl chlorophosphate, dimethyl chlorophosphate, diphenyl chlorophosphate, ethyl dichlorophosphate, phenyl dichlorophosphate, diethyl chlorophosphite or phosphorus oxytrichloride.

The phosphorylation reactions are carried out under basic conditions, preferably using one equivalent of triethylamine or pyridine in an inert solvent such as, for example, dichloromethane or toluene at elevated temperature, in particular at the boiling temperature of the solvent used.

In the case of the abovementioned dichloride and trichloride phosphorylating reagents, a hydrolysis step additionally follows the phosphorylation step. In the case of the abovementioned diethyl chlorophosphite, an oxidation step additionally follows the phosphorylation step.

Compounds of the formula I in which R1, R2 and R3 have the abovementioned meanings, R4 is cyano and A is —CH(OH)— can be prepared from corresponding compounds of the formula II by selective reduction of the carbonyl group.

The reduction of the carbonyl group in compounds of the formula II is carried out in a manner known to the person skilled in the art, preferably in suitable inert solvents such as 1,2-dimethoxyethane or an alcohol such as methanol, using a suitable reductant, such as, for example, sodium borohydride or lithium borohydride.

The preparation of compounds of the formula II in which R1, R2 and R3 have the meanings indicated above and R4 is cyano or hydrogen has already been described previously.

Compounds of the formula I in which R1, R2 and R3 have the abovementioned meanings, R4 is cyano, nitro or 1–4C-alkoxycarbonyl and A is oxygen (—O—), imino (—NH—), sulfinyl (—S(O)—) or sulfonyl (—S(O)$_2$—), can be prepared, for example, from compounds of the formula IV in which R1, R2 and R3 have the meanings indicated above and X is —CH$_2$CN, —CH$_2$NO$_2$ or —CH$_2$COOR (R=1–4C-alkyl) by reaction with suitably activated ethers, amines, sulfines or sulfones.

The reactions are preferably carried out in anhydrous inert solvents such as, for example, THF, DMF, DMSO or HMPT or mixtures thereof and, depending on the reactivity of the reagents employed, at temperatures between −30° and 100° C.

After deprotonation of the —CH$_2$CN, —CH$_2$NO$_2$ or the —CH$_2$COOR (R=1–4C-alkyl) group by a suitable base, ring formation is carried out by reaction with an ether, amine, sulfine or sulfone provided in the ω, ω'-position with suitable leaving groups. Suitable leaving groups which may be mentioned are in particular chlorine and bromine and reactive esterified hydroxyl groups (e.g. the toluenesulfonyloxy group).

Suitably activated ethers (1), amines (2), sulfines (3) and sulfones (4) which offer themselves are, for example, bis[2-(toluene-4-sulfonyloxy)ethyl] ether (1), N-benzyl-bis[2-(toluene-4-sulfonyloxy)ethyl]amine (2), bis[2-(toluene-4-sulfonyloxy)ethyl]-sulfine (3) and bis(2-chloroethyl) sulfone (4). (1) can be prepared according to C. Almensa, A. Moyano, F. Serratosa, Tetrahedron 1992, 48, 1497–1506, (2) or (3) can be prepared from the corresponding bis-hydroxy compounds N-benzyl-bis(2-hydroxyethyl)amine (Mamaew, Schischkin, J. Org. Chem. (USSR), Engl. Transl. 1966, 2, 584) or bis(2-hydroxyethyl)sulfine (Price, Bullit, J. Org. Chem. 1947, 12, 277) by ditosylation.

The temporarily introduced amine protective group (2) can be removed again after ring formation has taken place. Bis(2-chloroethyl) sulfone (4) is commercially available.

Compounds of the formula I in which R1, R2 and R3 have the meanings indicated above, R4 is 1–4C-alkoxy and A is oxygen (—O—) or imino (—NH—) can be obtained from the corresponding compounds of the formula I in which R4 is hydroxyl by reaction with suitable alkylating agents.

Compounds of the formula I in which R1, R2 and R3 have the meanings indicated above, R4 is hydroxyl and A is oxygen (—O—) or imino (—NH—) can be obtained, for example, from compounds of the formula IV in which R1, R2 and R3 have the meanings indicated above and X is lithium by reaction with tetrahydropyran-4-one or piperidin-4-one. Expediently, the piperidin-4-one is employed here in temporarily protected form, for example as N-benzylpiperidin-4-one, and the protective group is removed again, if desired, after reaction has taken place.

Compounds of the formula I in which R1, R2, R3 and R4 have the meanings indicated above, A is >C=N—R6 and R6 is hydroxyl can be obtained by reaction of the corresponding compounds of the formula II with hydroxylamine.

By further derivatizations of these oxime compounds, known to the person skilled in the art on the basis of his expert knowledge, those compounds of the formula I are accessible in which A is carbonylimino (by Beckmann rearrangement of the corresponding oxime compounds) or in which A is >C=N—R6 and R6 is 1–4C-alkylcarbonyloxy (by acylation of the corresponding oxime compounds).

The isolation and purification of the substances according to the invention is carried out in a manner known per se, for example in such a way that the solvent is distilled off in vacuo and the residue obtained is recrystallized from a suitable solvent or subjected to one of the customary purification methods, such as, for example, column chromatography on suitable support material.

Salts are obtained by dissolving the free compound in a suitable solvent, e.g. in a chlorinated hydrocarbon, such as methylene chloride or chloroform, or a low molecular weight aliphatic alcohol (ethanol, isopropanol) which contains the desired acid or base, or to which the desired acid or base is then added. The salts are obtained by filtration, reprecipitation, precipitation using a nonsolvent for the addition salt or by evaporation of the solvent. Salts obtained can be converted by alkalization or by acidification into the free compounds which, in turn, can be converted into salts. In this manner, pharmacologically intolerable salts can be converted into pharmacologically tolerable salts.

The following examples serve to illustrate the invention in greater detail without restricting it. Equally, further compounds of the formula I whose preparation is not explicitly described can be prepared in an analogous manner or in a manner familiar per se to the person skilled in the art using customary process techniques.

The abbreviation h stands for hour(s), min for minute(s), RT for room temperature, m.p. for melting point, DMSO for dimethyl sulfoxide, DMF for dimethylformamide, THF for tetrahydrofuran, HMPT for hexamethylphosphoric triamide, LDA for lithium diisopropylamide and TLC for thin-layer chromatography.

EXAMPLES

Final Products

1. Methyl cis- and trans-4-cyano-4-(2,3-dihydro-7-methoxybenzofuran-2-spiro-1'-cyclopentan-4-yl)cyclohexane-1-carboxylate 1.1 Methyl cis-4-cyano-4-(2,3-dihydro-7-methoxybenzofuran-2-spiro-1'-cyclopentan-4-yl)cyclohexane-1-carboxylate The dithiane compound (11.7 g, 27.4 mmol) prepared according to working procedure A1 is dissolved in absolute methanol (600 ml) together with mercury(II) chloride (30.6 g, 109.6 mmol) and treated with perchloric acid (70% strength, 25.2 ml). The mixture is heated under reflux for about 3 h. After cooling to RT, the reaction mixture is filtered through kieselguhr. The filtrate is diluted with 300 ml dichloromethane and washed twice with 300 ml half-concentrated $NaHCO_3$ solution (pH≈7). It is extracted further with $Na_2SO_3$ solution (5% strength, 300 ml) and additionally once with saturated NaCl solution. The combined organic phases are dried over $MgSO_4$, filtered and concentrated in vacuo. Further purification is carried out by means of flash chromatography [silica gel, petroleum ether/ethyl acetate (85:15)]. The title compound (6.4 g, 63.2% of theory) is obtained as a colorless solid by subsequent crystallization from ethyl acetate/petroleum ether. TLC, silica gel (glass plates), [petroleum ether/ethyl acetate (6:4)], $R_f$=0.42, m.p.: 145–147° C.

1.2 Methyl trans-4-cyano-4-(2,3-dihydro-7-methoxybenzofuran-2-spiro-1'-cyclopentan-4-yl)cyclohexane-1-carboxylate The trans methyl ester compound is obtained from the batch described under 1.1 as a colorless solid (1.95 g, 19.5% of theory). TLC, silica gel (glass plates), [petroleum ether/ethyl acetate (6:4)], $R_f$=0.52, m.p.: 146–147° C.

2. cis- and trans-4-Cyano-4-(2,3-dihydro-7-methoxybenzofuran-2-spiro-1'-cyclopentan-4-yl)cyclohexane-1-carboxylic acid 2.1 cis-4-Cyano-4-(2,3-dihydro-7-methoxybenzofuran-2-spiro-1'-cyclopentan-4-yl)cyclohexane-1-carboxylic acid The cis-carboxylic acid methyl ester compound (4 g, 10.8 mmol) prepared according to the working procedure 1.1 is dissolved in absolute methanol (200 ml) and treated with an aqueous KOH solution (3.0 g, 55.4 mmol in 25 ml of $H_2O$) at RT with stirring. The mixture is stirred at RT for 3 h and at 40° C. for 10 h. The reaction solution is then almost completely concentrated in vacuo. The residue is taken up in 2 N hydrochloric acid (50 ml) and extracted (2 times) with dichloromethane (50 ml). The organic phase is dried over $MgSO_4$, filtered and concentrated in vacuo. The title compound (3.55 g, 92.5% of theory) is obtained as colorless crystals. TLC, silica gel (glass plates), [petroleum ether/ethyl acetate (4:6)], $R_f$=0.30, m.p.: 205–206° C.

2.2 trans-4-Cyano-4-(2,3-dihydro-7-methoxybenzofuran-2-spiro-1'-cyclopentan-4-yl)cyclohexane-1-carboxylic acid The trans-carboxylic acid compound is prepared analogously to procedure 2.1 from the trans-carboxylic acid methyl ester (300 mg, 0.81 mmol), dissolved in methanol (15 ml) and a KOH solution (300 mg, in 5 ml of $H_2O$). The title compound (110 mg, 38% of theory) is obtained as a colorless solid. TLC, silica gel (glass plates), [petroleum ether/ethyl acetate (4:6)], $R_f$=0.31, m.p.: 204–205° C.

3. Methyl cis- and trans-4-cyano-4-(2,3-dihydro-7-methoxybenzofuran-2-spiro-4'-tetrahydropyran-4-yl) cyclohexane-1-carboxylate 3.1 Methyl cis-4-cyano-4-(2,3-dihydro-7-methoxybenzofuran-2-spiro4'-tetrahydropyran-4-yl) cyclohexane-1-carboxylate 6.5 g (14.6 mmol) 1-(2,3-Dihydro-7-methoxybenzofuran-2-spiro-4'-tetrahydropyran-4-yl)-4-[1,3]dithian-2-ylidene cyclohexanecarbonitrile (prepared analogously to starting compound A1 using compound B5 as starting material) are dissolved in 300 ml absolute methanol together with mercury (II) chloride (15.9 g, 58.8 mmol) and treated with perchloric acid (70% strength, 9.1 ml, 146.9 mmol). The mixture is heated under reflux for about 2 h. After cooling to RT, the reaction mixture is filtered through kieselguhr. The filtrate is diluted with 150 ml dichloromethane and washed twice with 150 ml half-concentrated NaHCO₃ solution (pH≈7). It is extracted further with Na₂SO₃ solution (5% strength, 150 ml) and additionally once with saturated NaCl solution. The combined organic phases are dried over MgSO₄, filtered and concentrated in vacuo. Further purification is carried out by means of flash chromatography [silica gel, petroleum ether/ethyl acetate (7:3)]. The title compound (3.1 g, 55% of theory) is obtained as a colorless solid. TLC, silica gel (glass plates), [petroleum ether/ethyl acetate (6:4)], $R_f$=0.51, m.p.: 152° C.

3.2 Methyl trans-4-cyano-4-(2,3-dihydro-7-methoxybenzofuran-2-spiro-4'-tetrahydropyran-4-yl)cyclohexane-1-carboxylate The trans methyl ester compound is obtained from the batch described unter 3.1 as a colorless solid (0.8 g, 14% of theory). TLC, silica gell (glass pates), [petroleum ether/ethyl acetate (6:4)], $R_f$=0.66, m.p.: 141° C.

4. cis-4-Cyano-4-(2,3-dihydro-7-methoxybenzofuran-2-spiro-4'-tetrahydropyran-4-yl)cyclohexane-1-carboxylic acid The cis-carboxylic acid methyl ester compound (1 g, 2.6 mmol) prepared according to the working procedure 3.1 is dissolved in absolute methanol/ethanol (80 ml/80 ml) and treated with an aqueous KOH solution (0.73 g KOH in 10 ml H₂O) at RT with stirring. The mixture is stirred at RT for 3 h and at 40° C. for 10 h. The reaction solution is then almost completely concentrated in vacuo. The residue is taken up in 2N hydrochloric acid (12.5 ml) and extracted (2 times) with dichloromethane (15 ml). The organic phase is dried over MgSO₄, filtered and concentrated in vacuo. The title compound (0.85 g, 88% of theory) is obtained as colorless crystals. TLC, silica gel (glass plates), [dichloromethane/methanol (95:5)], $R_f$=0.38, m.p. 228° C.

5. cis-4-Cyano-4-(2,3-dihydro-7-methoxybenzofuran-2-spiro-1'-cyclopentan-4-yl)cyclohexane-1-carboxamide The cis-carboxylic acid compound (200 mg, 0.56 mmol) prepared according to procedure 2.1 is dissolved in thionyl chloride (3 ml) and stirred at 50° C. for 1 h. The reaction solution is concentrated in vacuo and coevaporated (3 times) with toluene. The residue obtained is dissolved in absolute toluene (10 ml) and cooled to 0° C. Dry ammonia gas is then passed through the solution for 10 min. A colorless precipitate results which is deposited almost completely from the reaction medium while stirring for 30 min at RT. The precipitate is filtered off from the reaction solution and washed with diisopropyl ether. For further purification, it is suspended with diisopropyl ether and filtered off with suction again. After drying in a high vacuum, the title compound is obtained as a colorless solid (160 mg, 80.2% of theory). TLC, silica gel (glass plates), [dichloro-methane/methanol (20:1)], $R_f$=0.13, m.p.: 242–243° C.

6. cis-4-Cyano-4-(2,3-dihydro-7-methoxybenzofuran-2-spiro-4'-tetrahydropyran-4-yl)cyclohexane-1-carboxamide If, instead of the 2-spiro-1'-cyclopentyl-substituted starting compounds, the 2-spiro-4'-tetrahydropyranyl-substituted starting compounds (working procedure A5) are employed, the carboxylic acid derivative of the title compound is obtained analogously to working procedures A1, 1.1 and 2.1. 350 mg (0.94 mmol) of this carboxylic acid compound are taken up in absolute toluene (4 ml), treated with thionyl chloride (4 ml) and stirred at 50° C. for 1 h. The reaction solution is then concentrated in vacuo and coevaporated with toluene (3 times). The residue is dissolved in absolute toluene (10 ml) and dry ammonia gas is passed through the solution (10 min) at 0° C. After addition of diethyl ether, the title compound precipitates from the reaction solution. After filtering off and washing with diethyl ether (10 ml), the title compound (310 mg, 87% of theory) is obtained as colorless crystals. TLC, silica gel (glass plates), [dichloromethane/methanol (20:1)], $R_f$=0.43, m.p.: 243° C.

7. cis-4-Cyano-4-(2,3-dihydro-7-methoxybenzofuran-2-spiro-1'-cyclopentan-4-yl)cyclohexane-1-carboxylic acid hydroxylamide The benzylhydroxylamine compound (400 mg, 0.85 mmol) prepared according to procedure A2 is dissolved in methanol (20 ml), treated with palladium on carbon (10% Pd, 150 mg) and stirred for 30 min in a recycling hydrogenation unit under a hydrogen atmosphere of 1 bar. The solution is filtered off from the palladium carbon and concentrated in vacuo. Flash chromatography [dichloromethane/methanol (95:5)] yields the title compound (195 mg, 61% of theory) as colorless crystals. TLC, silica gel (glass plates), [dichloro-methane/methanol (95:5)], $R_f$=0.35, m.p.: 132–133° C.

8. cis-4-Cyano-4-(2,3-dihydro-7-methoxybenzofuran-2-spiro-1'-cyclopentan-4-yl)cyclohexyl-1-phenyl phosphate The cis-hydroxy compound (500 mg, 1.53 mmol) prepared according to working procedure A3 is dissolved in absolute pyridine/toluene (4 ml, 1:1) under a nitrogen atmosphere and monophenyl dichlorophosphate is added dropwise with stirring at RT. The mixture is then stirred under reflux for 2.5 h and cooled to RT. After addition of a 0.1 N NaOH solution (5 ml), the reaction solution is stirred at RT for a further 15 min. For working-up, it is acidified with 5 N HCl and extracted with ethyl acetate. The organic phase is dried using MgSO₄, filtered off and concentrated in vacuo. The residue thus obtained is purified by means of flash chromatography [dichloromethane/methanol/acetic acid (13:1:0.2)]. The title compound is obtained as colorless crystals (190 mg, 26% of theory). TLC, silica gel (glass plates), [dichloromethane/methanol/acetic acid (13:1:0.2)], $R_f$=0.20, m.p.: 104–105° C.

9. 4-a-Cyano-4-e-(2,3-dihydro-7-methoxybenzofuran-2-spiro-1'-cyclopentan-4-yl)tetrahydropyran 2,3-Dihydro-7-methoxybenzofuran-2-spiro-1'-cyclopentan-4-ylacetonitrile (1.5 g, 6.17 mmol), prepared according to working procedure B4) is dissolved in absolute THF (30 ml) at RT and HMPT (8 ml) is added. The solution is cooled to −30° C. under a nitrogen atmosphere. Fresh LDA, prepared from diisopropylamine (2.68 ml), n-butyllithium (12.75 ml of a 1.6 molar solution in toluene) and absolute THF (5 ml), is then slowly added dropwise to the reaction solution in a dropping funnel cooled with dry ice and the mixture is stirred at −30° C. for about 30 min. After slight warming to −20° C., a solution of bis[2-(toluene-4-sulfonyloxy)ethyl] ether (2.81 g, 6.77 mmol) [C. Almansa, A. Moyano, F. Serratosa, *Tetrahedron* 1992, 48, 1497–1506] in absolute THF (10 ml) is injected into the reaction mixture (→deep-red coloration) under a nitrogen countercurrent. The reaction solution is slowly warmed to about 0° C. (TLC checking) and then poured onto a half-concentrated aqueous ammonium chloride solution. The mixture is extracted (3 times) with ethyl acetate and concentrated after drying of the organic phase over MgSO₄ and filtration in vacuo. The solid residue is crystallized from ethyl acetate/petroleum ether. The desired product is obtained as colorless crystals (910 mg, 47% of theory). TLC, silica gel (glass plates), [petroleum ether/ethyl acetate (6:4)], $R_f$=0.63, m.p.: 154° C.

10. 4-a-Cyano-4-e-[2,3-dihydro-7-methoxybenzofuran-2-spiro-4'-tetrahydropyran-4-yl)tetrahydropyran 2,3-Dihydro-7-methoxybenzofuran-2-spiro-4'-tetrahydropyran-4-ylacetonitrile (1.5 g, 5.78 mmol, prepared according to working procedure A4) is dissolved in absolute THF (80 ml) at RT and HMPT (12.5 ml) is added. The solution is cooled to −30° C. under a nitrogen atmosphere. Fresh LDA, prepared from diisopropylamine (2.5 ml), n-butyllithium (12.0 ml of a 1.6 molar solution in toluene) and absolute THF (20 ml), is then slowly added dropwise to the reaction solution in a dropping funnel cooled with dry ice and the mixture is stirred at −30° C. for about 30 min. After slight warming to −20° C., a solution of bis[2-(toluene-4-sulfonyloxy)ethyl] ether (3.6 g, 8.7 mmol) [C. Almensa, A. Moyano, F. Serratosa, *Tetrahedron* 1992, 48, 1497–1506] in absolute THF (20 ml) is injected into the reaction mixture (→deep-red coloration) under a nitrogen countercurrent. The reaction solution is slowly warmed to about 0° C. (TLC checking) and then poured onto a half-concentrated aqueous ammonium chloride solution. It is extracted with ethyl acetate (3 times) and concentrated in vacuo after drying of the organic phase over $MgSO_4$ and filtration in vacuo. The solid residue is crystallized from ethyl acetate/petroleum ether. The desired title compound is obtained as colorless crystals (1.6 g, 84.1% of theory). TLC, silica gel (glass plates), [petroleum ether/ethyl acetate (6:4)], $R_f$=0.63, m.p.: 162.5° C.

11. 1,1-Dioxo-4-a-cyano-4-e-(2,3-dihydro-7-methoxybenzofuran-2-spiro-1'-cyclopentan-4-yl)tetrahydro-1-thiopyran 2,3-Dihydro-7-methoxybenzofuran-2-spiro-1'-cyclopentan-4-ylacetonitrile (636 mg, 2.6 mmol, prepared according to working procedure B4) is dissolved in absolute DMF (12 ml) at RT. Anhydrous $K_2CO_3$ (900 mg, 6.5 mmol, NaI (122 mg, 0.8 mmol) and bis(2-chloroethyl) sulfone (500 mg, 2.6 mmol) are then added and the mixture is stirred at 100° C. for 3 h under a nitrogen atmosphere. After complete conversion (TLC checking!), the reaction solution is allowed to cool to RT, the solid is filtered off and the filtrate is concentrated in vacuo. The residue is taken up in ethyl acetate and extracted (3 times) with water. The combined organic phases are dried over $MgSO_4$ and concentrated in vacuo. Further purification is carried out by flash chromatography [silica gel, petroleum ether/ethyl acetate (6:4)]. After crystallization from ethyl acetate/diisopropyl ether, the title compound (220 mg, 23.4% of theory) is obtained as a colorless solid. TLC, silica gel (glass plates), [toluene/acetone (8:2)], $R_f$=0.71, m.p.: 185–186° C.

12. 4-a-Hydroxy-4-e-(2,3-dihydro-7-methoxy-benzofuran-2-spiro-1'-cyclopentan-4-yl)tetrahydropyran The bromo compound (2.0 g, 7.0 mmol) prepared according to procedure B10 is dissolved in absolute THF (100 ml) under a nitrogen atmosphere, the solution is cooled to −70° C., a 1.6 molar solution of n-butyllithium in n-hexane (4.4 ml, 7.0 mmol) is injected and the mixture is stirred at this temperature for 1 h. After this, a solution of tetrahydropyran-4-one (660 µl, 7.0 mmol) in absolute THF (20 ml) is added dropwise, the mixture is stirred at −70° C. for a further hour, the reaction solution is allowed to warm slowly to −20° C. (about 1 h) and is warmed further to 10° C. in the course of 2 h. For working-up, the reaction mixture is poured onto a half-concentrated aqueous $NH_4Cl$ solution and extracted with ethyl acetate (2 times 100 ml). The organic phase is dried over $MgSO_4$, filtered off and concentrated in vacuo. Flash chromatography [silica gel, petroleum ether/ethyl acetate (1:1)] and subsequent crystallization from diethyl ether yields the title compound (1.55 g, 73.2% of theory) as a colorless solid. TLC, silica gel (glass plates), [petroleum ether/ethyl acetate (7:3)], $R_f$=0.20, m.p.: 98–99° C.

13. 4-a-Methoxy-4-e-(2,3-dihydro-7-methoxy-benzofuran-2-spiro-1'-cyclopentan-4-yl)tetrahydropyran The hydroxy compound (1.45 g, 4.8 mmol) prepared according to procedure 12 is dissolved in absolute DMF (20 ml), treated with NaH (170 mg, 5.75 mmol, 80% strength in paraffin) and the mixture is stirred at 5° C. for 1 h. A solution of methyl iodide (350 µl, 5.75 mmol) in absolute DMF (5 ml) is then added dropwise and the mixture is stirred at RT overnight. For working-up, it is diluted with ethyl acetate (20 ml) and extracted with water (5 times). The organic phase is dried over $MgSO_4$, filtered and concentrated in vacuo. Flash chromatography [silica gel, petroleum ether/ethyl acetate (8:2)] and subsequent crystallization from diisopropyl ether/petroleum ether yields the title compound (860 mg, 56.6% of theory) as a colorless solid. TLC, silica gel (glass plates), [petroleum ether/ethyl acetate (7:3)], $R_f$=0.68, m.p.: 94–95° C.

14. 4-a-Cyano-4-e-(2,3-dihydro-7-methoxybenzofuran-2-spiro-1'-cyclopentan-4-yl)cyclohexan-1-one oxime The keto compound (1 g, 3.02 mmol) prepared according to procedure B1 is dissolved in absolute ethanol (10 ml) and treated with absolute pyridine (5 ml) and hydroxylamine hydrochloride (1.1 g, 15.35 mmol) with stirring. The reaction solution is then heated under reflux for 1 h. For working-up, the reaction mixture is concentrated in vacuo and coevaporated with toluene (3 times). Further purification is carried out by flash chromatography [silica gel, petroleum ether/ethyl acetate (6:4)]. By means of further crystallization from diisopropyl ether, the title compound (700 mg, 94% of theory) is obtained as a colorless solid. TLC, silica gel (glass plates), [petroleum ether/ethyl acetate (6:4)], $R_f$=0.28, m.p.: 172–173° C.

15. 4-a-Cyano-4-e-(2,3-dihydro-7-methoxybenzofuran-2-spiro-1'-cyclopentan-4-yl)cyclohexan-1-one O-acetyl oxime The oxime compound (200 mg, 0.83 mmol) prepared according to procedure 14 is dissolved in absolute pyridine (1 ml) at RT and treated with acetic anhydride (0.2 ml). The reaction mixture is stirred at RT for 1 h. The solvent is then evaporated in vacuo and coevaporated three times with toluene. The residue obtained is taken up in ethyl acetate (20 ml) and washed with 2 N aqueous HCl (20 ml). The organic phase is dried over $MgSO_4$, filtered and concentrated in vacuo and the residue is crystallized from ethyl acetate/diisopropyl ether. The title compound (190 mg, 60% of theory) is obtained as colorless crystals. TLC, silica gel (glass plates), [petroleum ether/ethyl acetate (6:4)], $R_f$=0.43, m.p.: 192–193° C.

16. 7-Oxo-4-cyano-4-(2,3-dihydro-7-methoxy-benzofuran-2-spiro-1'-cyclopentan-4-yl)hexahydroazepine The oxime compound (500 mg, 1.47 mmol) prepared according to procedure 14 is dissolved in anhydrous pyridine (10 ml) with stirring, treated with p-toluenesulfonyl chloride (420 mg, 2.20 mmol) and stirred overnight at RT. The reaction solution is then diluted with dichloromethane (30 ml) and extracted with half-concentrated aqueous $NaHCO_3$ solution. The organic phase is dried using $MgSO_4$, filtered and concentrated in vacuo. The residue is taken up in formic acid (5 ml) and stirred at RT for 2 h. The formic acid is then concentrated in vacuo. Further purification is carried out by means of flash chromatography [silica gel, ethyl acetate]; the title compound is obtained as a colorless solid (320 mg, 64% of theory) by crystallization from diethyl ether/petroleum ether. TLC, silica gel (glass plates), ethyl acetate], $R_f$=0.17, m.p.: 195–196° C.

Starting Compounds

A1. 1-(2,3-Dihydro-7-methoxybenzofuran-2-spiro-1'-cyclopentan-4-yl)-4-[1,3]dithian-2-ylidene cyclohexanecarbonitrile 2-Trimethylsilyl-1,3-dithiane (15.5 ml, 81.8 mmol) is dissolved in absolute THF (400 ml) and cooled to −75° C. with stirring. A solution of n-butyllithium in n-hexane (51 ml, 81.8 mmol of a 1.6 molar solution) is then slowly added dropwise under a nitrogen atmosphere by means of a glass syringe and the mixture is stirred at −60° C. for a further 15 min. After cooling to −75° C. again, a solution of the keto compound (11.5 g, 35.34 mmol) prepared according to B1 in absolute THF (150 ml) is added dropwise during a period of 20 min. The mixture is stirred at −75° C. for 15 min, then slowly warmed (about 3 h) to RT. For working-up, the reaction solution is diluted with ethyl acetate (350 ml) and extracted (2 times) with 0.1 N hydrochloric acid (400 ml). The organic phase is dried using $MgSO_4$, filtered and concentrated in vacuo. The title compound (11.75 g, 77.9% of theory) is crystallized from diisopropyl ether. TLC, silica gel (glass plates), [petroleum ether/ethyl acetate (8:2)], $R_f$=0.69.

A2. cis-4-Cyano-4-(2,3-dihydro-7-methoxybenzofuran-2-spiro-1'-cyclopentan-4-yl)cyclohexane-1-carboxylic acid O-benzylhydroxylamide The carboxylic acid compound (400 mg, 1.12 mmol) prepared according to working procedure 2.1 is dissolved in absolute THF/DMF (40 ml, 3:1), O-benzylhydroxylamine hydrochloride (206 mg, 1.3 mmol) and diethyl cyanophosphonate (260 μl, 1.68 mmol) are added and the mixture is cooled to −15° C. with stirring. A solution of $Et_3N$ (280 μl, 2.0 mmol) in absolute THF (10 ml) is then slowly added dropwise, and the mixture is warmed to 0° C. and stirred for 2 h. The reaction solution is then poured onto a 5% strength aqueous $NaHCO_3$ solution (160 ml), extracted with ethyl acetate (3 times), dried over $MgSO_4$, filtered and evaporated in vacuo. The title compound thus obtained is crystallized in isopropanol as a colorless solid (400 mg, 77.5% of theory). TLC, silica gel (glass plates), dichloromethane/methanol (95:5)], $R_f$=0.58.

A3. cis-4-Cyano-4-(2,3-dihydro-7-methoxybenzofuran-2-spiro-1'-cyclopentan-4-yl)cyclohexan-1-ol Sodium borohydride (2.0 g, 52.4 mmol) is introduced into absolute methanol (70 ml) at RT with stirring. A suspension of the compound (6.3 g, 19.4 mmol) prepared according to B1 in absolute methanol (130 ml) is then added dropwise. After adding sodium borohydride (1.4 g, 36.7 mmol) again, the reaction mixture is treated with 2N hydrochloric acid until a pH of 2 is reached. A saturated sodium chloride solution (300 ml) and distilled water (100 ml) are added to the reaction solution and it is extracted with ethyl acetate (100 ml, 3 times). The combined organic phases are dried over magnesium sulfate and concentrated in vacuo after filtration. After flash chromatography on silica gel [petroleum ether/ethyl acetate (6:4)], the title compound (2.8 g) is obtained as a colorless solid. TLC, petroleum ether/ethyl acetate (6:4), $R_f$=0.29, m.p.: 143° C.

A4. 2,3-Dihydro-7-methoxybenzofuran-2-spiro-4'-tetrahydropyran-4-yl acetonitrile This compound is prepared analogously to compound B4 according to the working procedures B5–B9 by employing 3-chlorotetrahydropyran-4-one (prepared from tetrahydropyran-4-one and thionyl chloride) in working step B9 instead of 2-chlorocyclopentanone.

A5. 4-Cyano-4-(2,3-dihydro-7-methoxybenzofuran-2-spiro-4'-tetrahydropyran-4-yl)cyclohexanone This compound is prepared analogously to compound B1 according to the working procedures B2–B9, by employing 3-chlorotetrahydropyran-4-one (prepared from tetrahydropyran-4-one and thionyl chloride) in working procedure B9 instead of 2-chlorocyclopentanone.

B1. 4-Cyano-4-(2,3-dihydro-7-methoxybenzofuran-2-spiro-1'-cyclopentan-4-yl)cyclohexanone 0.6 g (1.56 mmol) of the compound prepared according to B2 is dissolved in a mixture of 1 ml of DMSO, 1 ml of distilled water and 0.5 g of sodium chloride and the solution is stirred at 180–185° C. for 10 h. After cooling the mixture, 200 ml of distilled water are added to the reaction solution and it is extracted with ethyl acetate, and the organic phase is separated off, dried over sodium sulfate and evaporated to dryness. After flash chromatography, 0.4 g of the title compound result as a yellowish solid of m.p. 92–94° C.

B2. Methyl 5-cyano-5-(2,3-dihydro-7-methoxybenzofuran-2-spiro-1'-cyclopentan-4-yl)-2-oxocyclohexane-carboxylate 0.25 g (0.82 mmol) of sodium hydride (80% strength in paraffin) is added in portions at RT under nitrogen to a solution of 1.2 g (0.29 mmol) of the compound prepared according to B3 in 25 ml of 1,2-dimethoxyethane, and the mixture is refluxed for 6 h, then allowed to cool to RT and stirred at RT for a further 48 h. 5 ml of methanol and 10 ml of 1N hydrochloric acid are then added, and after this the mixture is treated with 100 ml of distilled water and extracted with ethyl acetate. The organic phases are combined, dried over sodium sulfate and evaporated to dryness. By means of column chromatography, 0.6 g of the title compound is obtained as a white solid of m.p. 137–139° C.

B3. Methyl 4-cyano-4-(2,3-dihydro-7-methoxybenzofuran-2-spiro-1'-cyclopentan-4-yl)heptane-1,7-dicarboxylate A solution of 1.5 g (0.67 mmol) of the compound prepared according to B4 and 1 ml of Triton B in 50 ml of absolute acetonitrile is warmed to 60° C. for 10 min and 6 ml (0.66 mmol) of methyl acrylate is then added dropwise at this temperature. The solution is heated to reflux for 6 h. After cooling, the solvent is stripped off in a rotary evaporator, the residue is taken up in 150 ml of ethyl ether and the mixture is extracted by shaking with half-saturated sodium chloride solution. The organic phase is dried and the solvent is stripped off in a rotary evaporator. Column chromatography affords 2.0 g of the title compound as a yellow oil. TLC (petroleum ether/ethyl acetate 6:4), $R_f$=0.55.

B4. 2,3-Dihydro-7-methoxybenzofuran-2-spiro-1'-cyclopentan-4-ylacetonitrile 2.4 g (0.01 mol) of the compound prepared according to B5 are dissolved in 50 ml of absolute toluene and treated with 1 ml of fresh thionyl chloride with stirring. The mixture is refluxed for 1 h. After cooling to RT, the solvent is stripped off. The residue is then coevaporated a further 3 times together with 50 ml of toluene in each case. The residue is taken up in 30 ml of absolute toluene and slowly added dropwise at RT to a suspension of 0.5 g (0.01 mol) of sodium cyanide in 20 ml of absolute DMF and 1 ml of 18-crown-6. The mixture is stirred at RT for 4 h and then added to 200 ml of half-saturated sodium chloride solution and extracted with 200 ml of ethyl acetate. The organic phases are combined and dried over sodium sulfate. After flash chromatography, 1.9 g of the title compound are obtained as a brown oil. TLC (petroleum ether/ethyl acetate 6:4). $R_f$=0.83.

B5. (2,3-Dihydro-7-methoxybenzofuran-2-spiro-1'-cyclopentan-4-yl)methanol 1.8 ml (6.0 mmol) of sodium dihydrido-bis(2-methoxyethoxy)aluminate (SDMA) are added under nitrogen to 15 ml of toluene. 1.6 g (6.0 mmol) of the compound obtained according to B6 are dissolved in 10 ml of toluene and slowly added dropwise to the SDMA solution under a continuous stream of nitrogen. After all the solution has been added dropwise, the mixture is additionally stirred at RT for a further 30 min and the solvent is then evaporated in a rotary evaporator. 100 ml of distilled water are added to the residue and the mixture is extracted with 200 ml of ethyl acetate. The organic phases are combined, dried and evaporated. 1.2 g of a pale yellow oil are obtained, which by addition of n-pentane spontaneously begins to crystallize. TLC (petroleum ether/ethyl acetate 6:4), $R_f$=0.34.

B6. Methyl 2,3-dihydro-7-methoxybenzofuran-2-spiro-1'-cyclopentane-4-carboxylate 10.2 g of the compound prepared according to B7 are dissolved in 500 ml of anhydrous n-hexane and treated with about 5 g of Amberlyst 15. The mixture is stirred at RT for 3 days, filtered and concentrated. The residue is chromatographed on a silica gel column using ethyl acetate/petroleum ether (4:6), and the chromatographically pure fractions are combined, concentrated and dried in a high vacuum. 7.2 g of the title compound are obtained as a yellow oil.

B7. Methyl 2-cyclopenten-1-ylmethyl-3-hydroxy-4-methoxybenzoate 12.7 g of the compound prepared according to B8 are treated with 50 ml of quinoline and the mixture is stirred at 190° C. for 1 h. After cooling, it is treated with water, adjusted to pH 3 using 2N hydrochloric acid and extracted with ethyl acetate. The residue which remains after concentration of the solvent is chromatographed on a silica gel column using ethyl acetate/petroleum ether (4:6). The chromatographically pure fractions are concentrated and dried in a high vacuum. 10.2 g of the title compound are obtained as a yellow oil.

B8. Methyl 3-(2-methylenecyclopentyloxy)-4-methoxy-benzoate 28.5 g of methyltriphenylphosphonium bromide are suspended in 300 ml of anhydrous THF under nitrogen and the mixture is cooled to −40° C. 50 ml of n-Butyllithium (1.6 M) in n-hexane are then added dropwise with stirring. After stirring at −20 to −10° C. for 30 min, a solution of 20 g of the compound prepared according to B9 in 100 ml of abs. THF is added dropwise. After this, the mixture is allowed to warm to RT and stirred for a further 1 h. It is poured onto water and extracted with ethyl acetate. The oil remaining after concentration of the organic phase is chromatographed on a silica gel column using ethyl acetate/petroleum ether (4:6). The chromatographically pure fractions are combined, concentrated and dried in a high vacuum. 12.7 g of the title compound are obtained as a colorless oil.

B9. Methyl 4-methoxy-3-(2-oxocyclopentyloxy)benzoate 23.8 g of methyl 3-hydroxy-4-methoxybenzoate are dissolved in 200 ml of anhydrous DMF and the solution is treated with 35 g of potassium carbonate (ground) and 13 ml of 2-chlorocyclopentanone. The mixture is stirred at 60° C. for 3 h, then the solid is filtered off and the filtrate is concentrated in vacuo. The residue is chromatographed on a silica gel column using ethyl acetate/petroleum ether (4:6). The chromatographically pure fractions are combined, concentrated and dried in a high vacuum. 24.3 g of the title compound are obtained as a pale yellow oil.

B10. 4-Bromo-2,3-dihydro-7-methoxybenzofuran-2-spiro-1'-cyclopentane 9.0 g of Amberlyst 15 are added to a solution of 8.4 g (0.03 mol) of the compound prepared according to B11 in 100 ml of absolute toluene and the mixture is stirred at 100° C. for 10 h. After cooling the mixture, the H$^+$ ion exchanger is filtered off and washed with 100 ml of methanol. After stripping off the organic phase and column chromatography, 7.4 g of the title compound are obtained as a yellow oil. TLC (petroleum ether/ethyl acetate 6:4). $R_f$=0.72.

B11. 2-Cyclopent-1-enylmethyl-3-hydroxy-4-methoxybromo-benzene 52.1 ml (0.082 mol) of n-butyllithium are added dropwise under nitrogen at −89° C. to a suspension of 26.5 g (0.074 mol) of methyltriphenylphosphonium bromide in 200 ml of absolute THF. The mixture is then warmed to −30° C., the suspension going into solution. After cooling to −70° C. again, a solution of 19.2 g (0.067 mol) of the compound prepared according to B12 in 200 ml of absolute of THF is added dropwise under nitrogen. The mixture is then warmed to −10° C. and stirred at this temperature for 5 h. [TLC (petroleum ether/ethyl acetate, 6:4) $R_f$ (methylene compound)=0.81]. After warming to RT, the mixture is filtered from solids, and the filtrate is extracted by shaking with 3×200 ml of half-saturated sodium chloride solution and 2×200 ml of distilled water. After combining the organic phases, drying over sodium sulfate and evaporating to dryness, the residue is taken up in 50 ml of quinoline and stirred at 195–205° C. for 1 h. After cooling the solution, 400 ml of ethyl acetate are added and the quinoline is extracted by shaking with 4×200 ml of 2N hydrochloric acid. The organic phases are combined, dried over sodium sulfate and brought to dryness in a rotary evaporator. After column chromatography, a yield of 8.4 g of the title compound results as a red-brown oil. TLC (petroleum ether/ethyl acetate 6:4), $R_f$=0.65.

B12. 4-Methoxy-3-(2-oxocyclopentyloxy)bromobenzene 17.7 g (0.15 mol) of 2-chlorocyclopentanone and 41.4 g (0.3 mol) of potassium carbonate are added to a solution of 20 g (0.1 mol) of 3-hydroxy-4-methoxy-bromobenzene in 300 ml of absolute DMF and the mixture is stirred at RT for 12 h. After filtering off the solids, the filtrate is concentrated, the residue is taken up in 500 ml of ethyl acetate and the solution is extracted by shaking with 3×200 ml of distilled water. Column chromatography affords 21.1 g of the title compound as a brown oil. TLC (petroleum ether/ethyl acetate 6:4), $R_f$=0.47.

Commercial Utility

The compounds according to the invention have valuable pharmacological properties which make them commercially utilizable. As selective cyclic nucleotide phosphodiesterase (PDE) inhibitors (namely of type 4), they are suitable on the one hand as bronchial therapeutics (for the treatment of airway obstructions on account of their dilating action but also on account of their respiratory rate- or respiratory drive-increasing action) and for the elimination of erectile dysfunction on account of the vasodilating action, but on the other hand especially for the treatment of disorders, in particular of an inflammatory nature, e.g. of the airways (asthma prophylaxis), of the skin, of the intestine, of the eyes, of the central nervous system and of the joints which are mediated by mediators such as histamine, PAF (platelet-activating factor), arachidonic acid derivatives such as leukotrienes and prostaglandins, cytokines, interleukins, chemokines, alpha-, beta- and gamma-interferon, tumor necrosis factor (TNF) or oxygen free radicals and proteases. The compounds according to the invention here are distinguished by low toxicity, good enteral absorption (high bioavailability), great therapeutic breadth and the absence of significant side effects.

On account of their PDE-inhibiting properties, the compounds according to the invention can be employed as therapeutics in human and veterinary medicine, where they can be used, for example, for the treatment and prophylaxis of the following illnesses: acute and chronic (in particular inflammatory and allergen-induced) airway disorders of various origins (bronchitis, allergic bronchitis, bronchial asthma); dermatoses (especially of proliferative, inflammatory and allergic nature) such as, for example, psoriasis (vulgaris), toxic and allergic contact eczema, atopic eczema, seborrheic eczema, lichen simplex, sunburn, pruritus in the anogenital area, alopecia areata, hypertrophic scars, discoid lupus erythematosus, follicular and widespread pyodermias, endogenous and exogenous acne, acne rosacea and other proliferative, inflammatory and allergic skin disorders; disorders which are based on an excessive release of TNF and leukotrienes, i.e., for example, disorders of the arthritic type (rheumatoid arthritis, rheumatoid spondylitis, osteoarthritis and other arthritic conditions), disorders of the immune system (AIDS, multiple sclerosis), types of shock [septic shock, endotoxin shock, gram-negative sepsis, toxic shock syndrome and ARDS (adult respiratory distress syndrome)] and also generalized inflammations in the gastrointestinal region (Crohn's disease and ulcerative colitis); disorders which are based on allergic and/or chronic, faulty immunological reactions in the region of the upper airways (pharynx, nose) and the adjacent regions (paranasal sinuses, eyes), such as, for example, allergic rhinitis/sinusitis, chronic rhinitis/sinusitis, allergic conjunctivitis and also nasal polyps; but also diseases of the heart which can be treated by PDE inhibitors, such as, for example, cardiac insufficiency, or disorders which can be treated on account of the muscle-relaxant action of the PDE inhibitors, such as, for example, erectile dysfunction or colics of the kidneys and the ureters in connection with kidney stones, or alternatively disorders of the CNS, such as, for example, depressions or arteriosclerotic dementia.

The invention further relates to a method for the treatment of mammals, including humans, who are suffering from one of the abovementioned illnesses. The process comprises administering to the sick mammal a therapeutically efficacious and pharmacologically tolerable amount of one or more of the compounds according to the invention.

The invention furthermore relates to the compounds according to the invention for use in the treatment and/or prophylaxis of the illnesses mentioned.

The invention likewise relates to the use of the compounds according to the invention for the production of medicaments which are employed for the treatment and/or prophylaxis of the illnesses mentioned.

Furthermore, the invention relates to medicaments which contain one or more of the compounds according to the invention for the treatment and/or prophylaxis of the illnesses mentioned.

The medicaments are prepared by methods known per se which are familiar to the person skilled in the art. As medicaments, the compounds according to the invention (=active compounds) are either employed as such, or preferably in combination with suitable pharmaceutical auxiliaries, e.g. in the form of tablets, coated tablets, capsules, suppositories, patches, emulsions, suspensions, gels or solutions, the active compound content advantageously being between 0.1 and 95%.

The person skilled in the art is familiar on the basis of his expert knowledge with the auxiliaries which are suitable for the desired pharmaceutical formulations. Beside solvents, gel-forming agents, ointment bases and other active compound carriers, it is possible to use, for example, antioxidants, dispersants, emulsifiers, preservatives, solubilizers or permeation promoters.

For the treatment of disorders of the respiratory tract, the compounds according to the invention are preferably also administered by inhalation. For this purpose, these are either administered directly as a powder (preferably in micronized form) or by atomizing solutions or suspensions which contain them. With respect to the preparations and administration forms, reference is made, for example, to the details in European Patent 163 965.

For the treatment of dermatoses, the compounds according to the invention are applied, in particular, in the form of those medicaments which are suitable for topical application. For the production of the medicaments, the compounds according to the invention (=active compounds) are preferably mixed with suitable pharmaceutical auxiliaries and additionally processed to give suitable pharmaceutical formulations. Suitable pharmaceutical formulations which may be mentioned are, for example, powders, emulsions, suspensions, sprays, oils, ointments, fatty ointments, creams, pastes, gels or solutions.

The medicaments according to the invention are prepared by methods known per se. The dosage of the active compounds takes place in the order of magnitude customary for PDE inhibitors. Thus topical application forms (such as, for example, ointments) for the treatment of dermatoses contain the active compounds in a concentration of, for example, 0.1–99%. The dose for administration by inhalation is customarily between 0.01 and 1 mg per spray burst. The customary dose in the case of systemic therapy (p.o. or i.v.) is between 0.1 and 200 mg per administration.

Biological Investigations

In the investigation of PDE 4 inhibition at the cellular level, the activation of inflammatory cells has particular importance. As an example, the FMLP (N-formylmethionylleucylphenylalanine)-induced superoxide production of neutrophilic granulocytes may be mentioned, which can be measured as luminol-potentiated chemoluminescence [McPhail L C, Strum S L, Leone P A and Sozzani S, The neutrophil respiratory burst mechanism. In "Immunology Series" 1992, 57, 47–76; ed. Coffey R G (Marcel Decker, Inc., New York-Basel-Hong Kong)].

Substances which inhibit chemoluminescence and also cytokine secretion and the secretion of proinflammatory mediators from inflammatory cells, in particular neutrophilic and eosinophilic granulocytes, T lymphocytes, monocytes and macrophages, are those which inhibit PDE 4. This isoenzyme of the phosphodiesterase families is particularly represented in granulocytes. Its inhibition leads to an increase in the intracellular cyclic AMP concentration and thus to the inhibition of cellular activation. PDE 4 inhibition by the substances according to the invention is thus a central indicator of the suppression of inflammatory processes. (Giembycz M A, Could isoenzyme-selective phosphodiesterase inhibitors render bronchodilatory therapy redundant in the treatment of bronchial asthma? Biochem Pharmacol 1992, 3, 2041–2051; Torphy T J et al., Phosphodiesterase inhibitors: new opportunities for treatment of asthma. Thorax 1991, 46, 512–523; Schudt C et al., Zardaverine: a cyclic AMP PDE ¾ inhibitor. In "New Drugs for Asthma Therapy", 379–402. Birkhäuser Verlag Basel 1991; Schudt C et al., Influence of selective phosphodiesterase inhibitors on human neutrophil functions and levels of cAMP and Ca; Naunyn-Schmiedebergs Arch Pharmacol 1991, 344, 682–690; Nielson C P et al., Effects of selective phosphodiesterase inhibitors on polymorphonuclear leukocytes respiratory burst J. Allergy Clin Immunol 1990, 86, 801–808; Schade et al., The specific type 3 and 4 phosphodiesterase inhibitor zardaverine suppress formation of tumor necrosis factor by macrophages. European Journal of Pharmacology 1993, 230, 9–14).

Inhibition of PDE4 Activity

Methodology

The activity test was carried out according to the method of Bauer and Schwabe, which was adapted to microtiter plates (Naunyn-Schmiedeberg's Arch. Pharmacol. 311, 193–198, 1980). The PDE reaction takes place here in the first step. In a second step, the resulting 5'-nucleotide is cleaved to give the uncharged nucleoside by a 5'-nucleotidase of the snake venom from Crotalus atrox. In the third step, the nucleoside is separated from the remaining charged substrate on ion exchange columns. Using 2 ml of 30 mM ammonium formate (pH 6.0), the columns are eluted directly into minivials to which is additionally added 2 ml of scintillator fluid for counting.

The inhibitory values determined for the compounds according to the invention [inhibitory concentrations as –log $IC_{50}$ (mol/l)] follow from Table A below, in which the numbers of the compounds correspond to the numbers of the examples.

TABLE A

| Compound | –log $IC_{50}$ |
| --- | --- |
| 2.1 | 8.22 |
| 4 | 7.69 |
| 5 | 8.31 |
| 6 | 7.65 |
| 7 | 7.52 |
| 8 | 7.44 |
| 9 | 8.26 |
| 11 | 7.72 |
| 13 | 7.41 |
| 14 | 7.78 |
| 16 | 7.96 |

We claim:

1. A compound of formula I

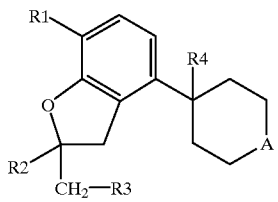

(I)

in which
R1 is 1–6C-alkoxy, 3–7C-cycloalkoxy, 3–7C-cycloalkylmethoxy, benzyloxy or 1–4C-alkoxy wherein more than half of the available hydrogen atoms are replaced by fluorine,
R2 is 1–4C-alkyl and
R3 is hydrogen or 1–4C-alkyl,
or in which
R2 and R3, together and including the two carbon atoms to which they are bonded, are a spiro-linked 5-, 6- or 7-membered hydrocarbon ring, optionally interrupted by an oxygen atom or an imino (—NH—) group,
R4 is hydrogen, hydroxyl, nitro, cyano, carboxyl, 1–4C-alkoxy or 1–4C-alkoxycarbonyl, A is B, —CH(R5)— or >C=N—R6, where
B is oxygen (—O—), amino (—NH—), sulfinyl (—S(O)—), sulfonyl (—S(O)$_2$—) or carbonylimino (—C(O)NH—) and
R5 is aminocarbonyl, mono- or di-1–4C-alkylaminocarbonyl, hydroxylaminocarbonyl (—C(O)NHOH), 1–4C-alkoxyaminocarbonyl or a radical of formula (a)

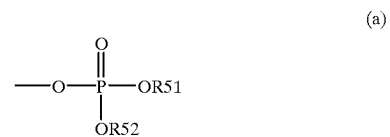

(a)

where
R51 is hydrogen, 1–4C-alkyl or aryl and
R52 is hydrogen, 1–4C-alkyl or aryl,
where aryl is a phenyl, pyridyl, benzyl or phenethyl radical which can be unsubstituted or mono- or disubstituted by hydroxyl, 1–4C-alkoxy, halogen, amino, cyano or nitro,
R6 is hydroxyl or 1–4C-alkylcarbonyloxy,
or a salt thereof.

2. A compound of formula I

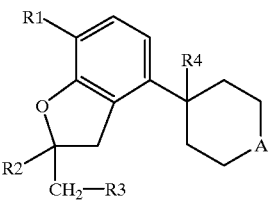

(I)

in which
R1 is 1–6C-alkoxy, 3–7C-cycloalkoxy, 3–7C-cycloalkylmethoxy, benzyloxy or 1–4C-alkoxy wherein more than half of the available hydrogen atoms are replaced by fluorine,
R2 is 1–4C-alkyl and
R3 is hydrogen or 1–4C-alkyl,
or in which
R2 and R3, together and including the two carbon atoms to which they are bonded, are a spiro-linked 5-, 6- or 7-membered hydrocarbon ring, optionally interrupted by an oxygen atom or an imino (—NH—) group,
R4 is hydroxyl or 1–4C-alkoxy,
A is —CH(R5)—, where
R5 is carboxyl or 1–4C-alkoxycarbonyl,
or a salt thereof.

3. A compound of formula I as claimed in claim 1, in which
R1 is 1–6C-alkoxy, 3–7C-cycloalkoxy, 3–7C-cycloalkylmethoxy, benzyloxy or 1–4C-alkoxy wherein more than half of the available hydrogen atoms are replaced by fluorine,
R2 is 1–4C-alkyl and
R3 is hydrogen or 1–4C-alkyl,
or in which
R2 and R3, together and including the two carbon atoms to which they are bonded, are a spiro-linked 5-, 6- or 7-membered hydrocarbon ring, optionally interrupted by an oxygen atom or an imino (—NH—) group, R4 is hydrogen, hydroxyl, nitro, cyano, carboxyl, 1–4C-alkoxy or 1–4C-alkoxycarbonyl, A is B, —CH(R5)— or >C=N—R6, where B is oxygen (—O—), amino (—NH—), sulfinyl (—S(O)—), sulfonyl (—S(O)$_2$—) or carbonylimino (—C(O)NH—) and R5 is aminocarbonyl, hydroxylaminocarbonyl (—C(O)NHOH), 1–4C-alkoxyaminocarbonyl or a radical of formula (a)

$$-\!\!\operatorname{O}-\!\!\underset{\underset{\text{OR52}}{|}}{\overset{\overset{\text{O}}{\|}}{\text{P}}}-\!\!\text{OR51} \qquad (a)$$

where

R51 is hydrogen, 1–4C-alkyl or aryl and

R52 is hydrogen, 1–4C-alkyl or aryl, where aryl is a phenyl or benzyl radical which can be unsubstituted or mono- or disubstituted by 1–4C-alkoxy, halogen or nitro, R6 is hydroxyl or 1–4C-alkylcarbonyloxy, or a salt thereof.

4. A compound of formula I as claimed in claim 3, in which

R1 is 1–4C-alkoxy, 3–5C-cycloalkoxy, 1–2C-alkoxy wherein more than half of the available hydrogen atoms are replaced by fluorine, R2 is 1–4C-alkyl and R3 is hydrogen or 1–4C-alkyl, or in which R2 and R3, together and including the two carbon atoms to which they are bonded, are a spiro-linked cyclopentane, cyclohexane, tetrahydrofuran or tetrahydropyran ring, R4 is hydrogen, hydroxyl, cyano, carboxyl, 1–2C-alkoxy or 1–2C-alkoxycarbonyl, A is B, —CH(R5)— or >C=N—R6, where B is oxygen (—O—), sulfinyl (—S(O)—), sulfonyl (—S(O)$_2$—) or carbonylimino (—C(O)NH—) and R5 is aminocarbonyl, hydroxylaminocarbonyl (—C(O)NHOH) or a radical of formula (a)

$$-\!\!\operatorname{O}-\!\!\underset{\underset{\text{OR52}}{|}}{\overset{\overset{\text{O}}{\|}}{\text{P}}}-\!\!\text{OR51} \qquad (a)$$

where

R51 is hydrogen, 1–2C-alkyl or aryl and

R52 is hydrogen, 1–2C-alkyl or aryl, where aryl is a phenyl or benzyl radical which can be unsubstituted or monosubstituted by methoxy or halogen, R6 is hydroxyl or 1–2C-alkylcarbonyloxy, or a salt thereof.

5. A compound of formula I as claimed in claim 3, in which

R1 is 1–4C-alkoxy,

R2 and R3, together and including the two carbon atoms to which they are bonded, are a spiro-linked cyclopentane or tetrahydropyran ring, R4 is hydroxyl, cyano or methoxy, A is B, —CH(R5)— or >C=N—R6, where B is oxygen (—O—), sulfonyl (—S(O)$_2$—) or carbonylimino (—C(O)NH—) and R5 is aminocarbonyl, hydroxylaminocarbonyl or a radical of the formula (a)

$$-\!\!\operatorname{O}-\!\!\underset{\underset{\text{OR52}}{|}}{\overset{\overset{\text{O}}{\|}}{\text{P}}}-\!\!\text{OR51} \qquad (a)$$

where

R51 is phenyl,

R52 is hydrogen,

R6 is hydroxyl or acetoxy, or a salt thereof.

6. Compounds of formula I as claimed in claim 3, in which

R1 is methoxy and

R2 and R3, together and including the two carbon atoms to which they are bonded, are a spiro-linked cyclopentane or tetrahydropyran ring, R4 is cyano or methoxy, A is B, —CH(R5)— or >C=N—R6, where B is oxygen (—O—), sulfonyl (—S(O)$_2$—) or carbonylimino (—C(O)NH—) and R5 is aminocarbonyl, hydroxylaminocarbonyl or a radical of the formula (a)

$$-\!\!\operatorname{O}-\!\!\underset{\underset{\text{OR52}}{|}}{\overset{\overset{\text{O}}{\|}}{\text{P}}}-\!\!\text{OR51} \qquad (a)$$

where

R51 is phenyl,

R52 is hydrogen,

R6 is hydroxyl, or a salt thereof.

7. A medicament composition comprising a customary pharmaceutical acceptable carrier and an effective amount of a compound as claimed in claim 1.

8. In a method for producing a medicament composition comprising combining an effective amount of active ingredient for treating an airway disorder and a customary pharmaceutical auxiliary and/or excipient, the improvement wherein the active ingredient is a compound of formula I as claimed in claim 1 or a pharmaceutically-acceptable salt thereof.

9. In a process which comprises administering an effective amount of active ingredient to a subject afflicted with an airway disorder, the improvement wherein the active ingredient is a compound of formula I according to claim 1 or a pharmaceutically-acceptable salt thereof.

10. A medicament composition comprising a pharmaceutically acceptable carrier and an effective amount of a compound as claimed in claim 1.

11. In a method for compounding a medicament composition comprising combining an effective amount of active ingredient for treating an airway disorder and a pharmaceutically acceptable carrier, the improvement wherein the active ingredient is a compound of formula I as claimed in claim 2 or a pharmaceutically-acceptable salt thereof.

12. In a method which comprises administering an effective amount of active ingredient to a subject afflicted with an airway disorder, the improvement wherein the active ingredient is a compound of formula I according to claim 2 or a pharmaceutically-acceptable salt thereof.

13. A medicament composition comprising a pharmaceutically acceptable carrier and an effective amount of a compound as claimed in claim 3.

14. A method for producing a medicament composition which comprises combining an effective amount of active ingredient for treating an airway disorder and a pharmaceutically acceptable carrier, wherein the active ingredient is a compound of formula I as claimed in claim 3 or a pharmaceutically-acceptable salt thereof.

15. A process for treating a subject afflicted with an airway disorder, which comprises administering an effective amount of active ingredient to the subject and wherein the active ingredient is a compound of formula I according to claim 3 or a pharmaceutically-acceptable salt thereof.

\* \* \* \* \*